United States Patent [19]

Labovitz et al.

[11] Patent Number: 4,561,881
[45] Date of Patent: Dec. 31, 1985

[54] POLLEN SUPPRESSANT COMPRISING A PYRIDAZOLYLAMINE

[75] Inventors: Jeffrey N. Labovitz, Palo Alto; Lawrence Fang, Daly City, both of Calif.

[73] Assignee: Lafarge Coppee, Paris, France

[21] Appl. No.: 532,094

[22] Filed: Sep. 14, 1983

[51] Int. Cl.$^4$ .................. A01N 43/58; C07D 237/34; C07D 403/04; C07D 401/12
[52] U.S. Cl. .................................. 71/92; 71/93; 544/182; 544/183; 544/184; 544/218; 544/219; 544/235; 544/236; 544/237; 544/238; 544/239
[58] Field of Search ............ 71/92, 93; 544/238, 544/239, 182, 183, 184, 218, 219, 235, 236, 237

[56] References Cited

U.S. PATENT DOCUMENTS 3,967,952 7/1976 Abdulla et al. .................. 544/239

Primary Examiner—Mark L. Berch
Attorney, Agent, or Firm—Oblon, Fisher, Spivak, McClelland & Maier

[57] ABSTRACT

A pollen suppressant of the formula

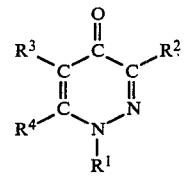

wherein $R^1$ and $R^4$ independently represent $C_1$–$C_4$ alkyl, phenyl, naphthyl, or phenyl or naphthyl substituted with one to three substituents selected from the group consisting of halogen, trihalomethyl, $C_1$–$C_4$ alkoxy, $C_1$–$C_4$ alkyl, and cyano; $R^2$ is

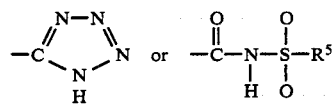

where $R^5$ is a $C_1$–$C_{12}$ alkyl group, optionally substituted with one or more halogen atoms, or an aryl group selected from the group consisting of 6-membered rings containing 0–3 nitrogens and fused bicyclic 10-membered rings containing 6 atoms in each ring and 0–3 nitrogens per ring with the remaining atoms in the ring or rings of said aryl group being carbon atoms, said aryl group being optionally substituted with a $C_1$–$C_4$ alkyl group or an electron-withdrawing group, $R^3$ is hydrogen, a halogen a $C_1$–$C_4$ alkyl group, a carboxy group or an agronomically acceptable alkali metal salt thereof, or a group of the formula —$COOR^6$ or —$CONR^6R^7$ where $R^6$ is a $C_1$–$C_4$ alkyl group and $R^7$ is $R^6$ or hydrogen, is disclosed along with methods of producing these compounds and of using them to produce hybrid seeds in self-fertilizing plants.

37 Claims, No Drawings 4,561,881

POLLEN SUPPRESSANT COMPRISING A PYRIDAZOLYLAMINE

BACKGROUND OF THE INVENTION

1. Field of the Invention

The present invention relates to a series of pyridazinone compounds, a process for their preparation, compositions containing these compounds, and a method of regulating the growth of plants using such compounds.

2. Description of the Prior Art

Although genetic manipulation of plants through cross-breeding is a well-known process, hybrids of self-pollinating plants had been difficult to produce. In some cases, e.g., corn, intensive hand labor is required to prevent self-pollinating but is possible because the male and female flower parts are distant from each other on the corn stalk. However, in other plants, e.g., wheat, the male and female plant parts are contained within the same flower and self-pollination is difficult if not impossible to prevent. In wheat, the male stamen produces pollen inside a closed flower. The pollen then falls within the closed flower onto the female stigma. Only after this self-pollination step does the flower open to release extra pollen. Mechanical prevention of self-pollination as is practiced in corn is accordingly impossible in a plant such as wheat.

Nevertheless, it is possible to inhibit self-pollination in wheat and similar plants by chemically inhibiting the formation of pollen or by inducing the plant to produce non-functioning pollen. Several compounds have previously been developed which produce these effects.

DOS No. 28 08 795 discloses compounds of the formula:

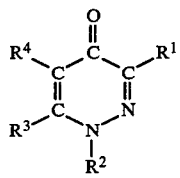

in which $R^1$ is carboxy, a carboxy salt, or an alkoxy carbonyl group, $R^2$ is a substituted phenyl group, $R^3$ is alkyl, and $R^4$ is hydrogen, alkyl or halogen. These compounds are disclosed to be pollen suppressants.

Published European patent application No. 0 037 133 discloses compounds of the formula:

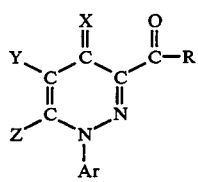

in which X represents oxygen or sulfur, Y represents hydrogen, halogen or an alkyl group, Z represents an alkyl group, Ar represents an optionally substituted phenyl group, and R represents a group which may be, among others $NR^1R^2$ or $ONR^1R^2$ in which $R^1$ can be hydrogen and $R^2$ can be an alkoxy group, an acyl group derived from a carboxylic or carbamic acid, or an alkyl group substituted with a carboxylic acid or ester group. These compounds are also disclosed to be pollen suppressants.

Published European patent application No. 0 049 971 discloses compounds of the formula:

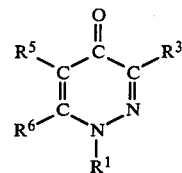

in which $R^1$ can be phenyl substituted with a halogen, $R^3$ can be carboxy or an alkali metal salt thereof, an alkoxy carbonyl, or a substituted carbamoyl, $R^5$ is a carboxy derivative of the type defined for $R^3$, and $R^6$ is a $C_1$-$C_4$ alkyl group. These compounds are disclosed to be chemical hybridizing agents which operate by causing male plant sterility.

Nevertheless, many of these compounds have adverse affects on hybrid seed quality or injure plants at doses only slightly above those required to produce maximum male plant sterility. Accordingly, a continued need for new pollen suppressants useful for producing hybrid seed of cereal grain exists.

SUMMARY OF THE INVENTION

Accordingly, it is an object of this invention to provide chemical sterilants for producing hybrid seed of cereal grain plants.

It is a further object of this invention to provide a method of suppressing pollen production in cereal grain plants using these compounds.

It is still a further object of this invention to provide a method for producing hybrid seed of cereal grain plants using the novel chemical sterilants of the invention.

These and other objects of the invention as will hereinafter become more readily apparent have been accomplished by providing a chemical pollen suppressant of the formula:

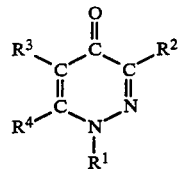

wherein $R^1$ and $R^4$ independently represent $C_1$-$C_4$ alkyl, phenyl, naphthyl, or phenyl or naphthyl substituted with one to three substituents selected from the group consisting of halogen, trihalomethyl, $C_1$-$C_4$ alkoxy, $C_1$-$C_4$ alkyl, and cyano;

$R_2$ is

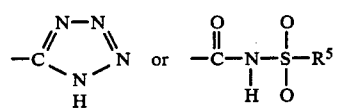

where $R^5$ is a $C_1$-$C_{12}$ alkyl group, optionally substituted with one or more halogen atoms, or an aryl group selected from the group consisting of 6-membered rings containing 0–3 nitrogens and fused bicyclic 10-membered rings containing 6 atoms in each ring and 0–3 nitrogens per ring with the remaining atoms in the ring or rings of said aryl group being carbon atoms, said aryl group being optionally substituted with a $C_1$–$C_4$ alkyl group or an electron-withdrawing group;

$R^3$ is hydrogen, a halogen, a $C_1$–$C_4$ alkyl group, a carboxy group or an agronomically acceptable alkali metal salt thereof, or a group of the formula —$COOR^6$ or —$CONR^6R^7$ where $R^6$ is a $C_1$–$C_4$ alkyl group and $R^7$ is $R^6$ or hydrogen.

DESCRIPTION OF THE PREFERRED EMBODIMENTS

The present invention provides novel pyridazoylamines in which $R^2$, the substituent at the 3-position of the pyridazinone ring, is not a substituent normally used in pollen supressants. Instead, $R^2$ is a tetrazole or a sulfonamidocarboxy group. Thus, the chemical pollen suppressants of the invention include those compounds having the formula:

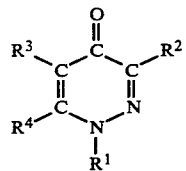

wherein $R^1$ and $R^4$ independently represent $C_1$–$C_4$ alkyl, phenyl, naphthyl, or phenyl or naphthyl substituted with one to three substituents selected from the group consisting of halogen, trihalomethyl, $C_1$–$C_4$ alkoxy, $C_1$–$C_4$ alkyl, and cyano;

$R^2$ is

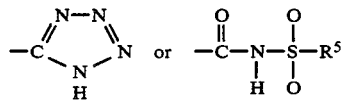

where $R^5$ is a $C_1$–$C_{12}$ alkyl group, optionally substituted with one or more halogen atoms, or an aryl group selected from the group consisting of 6-membered rings containing 0–3 nitrogens and fused bicyclic 10-membered rings containing 6 atoms in each ring and 0–3 nitrogens per ring with the remaining atoms in the ring or rings of said aryl group being carbon atoms, said aryl group being optionally substituted with a $C_1$–$C_4$ alkyl group or an electron-withdrawing group; and $R^3$ is hydrogen, a halogen, a $C_1$–$C_4$ alkyl group, a carboxy group or an agronomically acceptable alkali metal salt thereof, or a group of the formula —$COOR^6$ or —$CONR^6R^7$ where $R^6$ is a $C_1$–$C_4$ alkyl group and $R^7$ is $R^6$ or hydrogen.

Preferred substituents are those in which $R^1$ represents phenyl or phenyl substituted with one to three substituents selected from the group consisting of halogen, trihalomethyl, $C_1$–$C_4$ alkoxy, $C_1$–$C_4$ alkyl and cyano; more preferably by phenyl substituted with one of said substituents; even more preferably by phenyl substituted with one halogen atom; and most preferably by phenyl substituted with chlorine in the para position; $R^2$ is

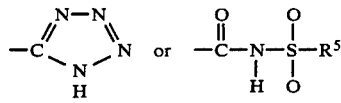

wherein $R^5$ is a $C_1$–$C_{12}$ alkyl group or an aryl group either of which is unsubstituted or is substituted with a $C_1$–$C_4$ alkyl, $NO_2$, CN, $COR^6$, CHO, COOH, $COOR^6$, halogen, or $CONR^6R^7$ group and further if an aryl group is preferred to be a phenyl, naphthyl, pyridyl, or naturally occurring purine or pyrimidine group which preferably is unsubstituted, $R^5$ is more preferably a $C_1$–$C_{12}$ alkyl group, even more preferably a $C_1$–$C_8$ alkyl group, and most preferably a $C_1$–$C_4$ alkyl group, which optionally is substituted with one or more halogen atoms, preferably fluorine;

$R^3$ is hydrogen; and $R^4$ is a $C_1$–$C_4$ alkyl group, most preferably a methyl group.

Preferred compounds are defined by selecting one or more of these listings of preferred substituents in combination with the general formula previously given. Certain combinations of substituents are especially preferred. One preferred grouping occurs when $R^1$ is phenyl mono-substituted with a halogen, $R^2$ is

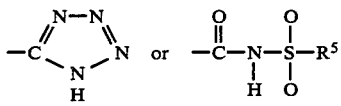

in which $R^5$ is a $C_1$–$C_{12}$ alkyl group optionally substituted with one or more halogen atoms or a phenyl, naphthyl, or pyridyl group, optionally substituted with one or more $C_1$–$C_4$ alkyl or specifically named electron-withdrawing groups, $R^3$ is hydrogen and $R^4$ is methyl.

Also included within the scope of the invention are agronomically acceptable acid addition salts of compounds having the general formula given. Typical acid addition salts are those formed with strong acids such as hydrochloric, hydrobromic, sulfuric, and nitric acids. Also included are compounds in which the hydrogen on the nitrogen of $R^2$ is replaced with a sodium or potassium ion. Since this hydrogen is more active than the hydrogen of a typical amide, such salts may be prepared by the action of a strong base, such as sodium hydroxide or potassium hydroxide, on a compound of the general formula given. Salts of acidic or basic functional groups in other substituents are also included in this invention.

Typical compounds of the invention include the following:

1-phenyl-1,4-dihydro-3-tetrazolyl-4-oxo-6-methylpyridazine 1-phenyl-1,4-dihydro-3-chloromethylsulfonamidocarbonyl-4-oxo-6-ethylpyridazine 1-phenyl-1,4-dihydro-3-phenylsulfonamidocarbonyl-4-oxo-6-phenylpyridazine 1-(4-chlorophenyl)-1,4-dihydro-3-trichloromethylsulfonamidocarbonyl-4-oxo-6-methylpyridazine 1-(4-bromophenyl)-1,4-dihydro-3-(4-pyridylsulfonamidocarbonyl)-4-oxo-6-ethylpyridazine-5-carboxylic acid 1-(3,4-dichlorophenyl)-1,4-dihydro-3-tetrazolyl-4-oxo-6-propylpyridazine 1-(4-iodophenyl)-1,4-dihydro-3-(2,4-dinitrophenylsulfonamidocarbonyl)-4-oxo-6-butylpyridazine
1-(4-fluorophenyl)-1,4-dihydro-3-(8-purinylsulfonamidocarbonyl)-4-oxo-6-butylpyridazine
1-(4-chlorophenyl)-1,4-dihydro-3-naphthylsulfonamidocarbonyl-4-oxo-6-phenylpyridazine
1-(3-chlorophenyl)-1,4-dihydro-3-tetrazolyl-4-oxo-6-methylpyridazine
1-(2,4,6-trichlorophenyl)-1,4-dihydro-3-[8-(2-amino-6-oxypurinyl)sulfonamidocarbonyl]-4-oxo-6-phenylpyridazine
1-(4-methylphenyl)-1,4-dihydro-3-(n-butylsulfonamidocarbonyl)-4-oxo-6-phenylpyridazine
1-(4-trifluoromethylphenyl)-1,4-dihydro-3-trifluoromethylsulfonamidocarbonyl-4-oxo-6-methyl-pyridazine
1-(3-ethoxyphenyl)-1,4-dihydro-3-dodecylsulfonamidocarbonyl-4-oxo-6-ethylpyridazine
1-(3-cyanophenyl)-1,4-dihydro-3-(4-carboxyphenylsulfonamidocarbonyl)-4-oxo-6-butylpyridazine
1-(2-chloro-4-methylphenyl)-1,4-dihydro-3-(3-propanoylphenylsulfonamidocarbonyl-4-oxo-6-phenylpyridazine
1-(2-trifluoromethyl-4-chlorophenyl)-1,4-dihydro-3-(4-t-butyloxycarbonylphenylsulfonamidocarbonyl)-4-oxo-6-methylpyridazine
1-(2-trifluoromethyl-4-bromophenyl)-1,4-dihydro-3-(2,6-dichlorophenylsulfonamidocarbonyl)-4-oxo-6-ethylpyridazine- 3-carboxylic acid
1-(2-chloro-5-trifluoromethylphenyl)-1,4-dihydro-3-trichloromethylsulfonamidocarbonyl-4-oxo-6-ethylpyridazine-5-carboxylic acid
1-(2-naphthyl)-1,4-dihydro-3-(4-cyanophenylsulfonamidocarbonyl)-4-oxo-6-butylpyridazine-5-carboxylic acid and the sodium, potassium, and lithium carboxylate, amide, and pseudo amide salts of each of the above compounds and the acid addition salts of all the above listed compounds. By carboxylate salt is meant a salt of a carboxylate group at C-5, by amide salt is meant a salt of either an amide group at C-5 or of a sulfonamido group at C-3, and by pseudo amide salt is meant a salt of a tetrazolyl group at C-3. By acid addition salt is meant a salt formed by the protonation of a ring or side chain nitrogen.

The compounds in the invention can be synthesized according to known methods for the production of analogous compounds or can be produced by synthetic modification of known pyridazinones. For examples, one suitable method involves the reaction of a 4-hydroxy-2-pyrone of the formula:

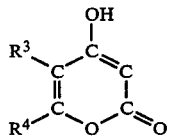

in which $R^3$ and $R^4$ represents one of the groups previously named, with a diazonium salt, for example, a diazonium chloride, prepared from an amine of the formula $R^1NH_2$ where $R^1$ has the meaning previously defined. The reaction is carried out by reacting the pyrone with one equivalent of an aqueous base, such as potassium or sodium hydroxide, acetate, or carbonate, generally at a temperature of from $-10°-50°$ C. in a polar solvent, such as water, methanol, ethanol, or dimethyl formamide. A product having the following formula is obtained:

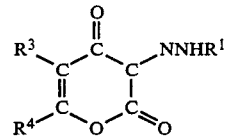

wherein $R^1$, $R^3$ and $R^4$ have the previously given meanings. Upon heating at a temperature of from 20° to 150° C. (preferably 40° to 100° C.) in an aqueous solution of acid or base, such as hydrochloric acid, trifluoroacetic acid, sulfuric acid, methanesulfonic acid, nitric acid, sodium carbonate, or sodium hydroxide, a pyridazinone of the formula:

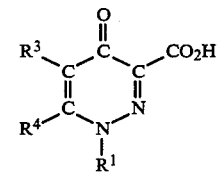

is obtained, where $R^1$, $R^3$, and $R^4$ have the meanings previously defined.

Another suitable synthetic technique is described by Plesica et al, *J. Heterocyclic Chem.*, 18, 333–334 (1981), which is herein incorporated by reference. This method, which involves reaction of an azo derivative of β-dicarbonyl compounds with dimethylformamide dimethylacetal to yield 3-carboxypyridazinones, gives compounds of the desired formula and can be modified to provide a variety of substituents by selection of the starting materials.

The above-indicated 3-carboxypyridazinone can then be converted into compounds of the invention by known methods. For example, the carboxylic acid group can be converted into a mixed acid anhydride, for example by reacting with ethylchloroformate. The acid anhydride is then converted into an amide by reacting the acid anhydride with concentrated ammonia. The amide is then converted into a sulfonamide by reacting with a alkyl- or arylsulfonyl chloride. The product sulfonamide can also be prepared by reacting the mixed anhydride directly with an excess of an anion of the alkyl- or arylsulfonamide, and preparation by this method is preferred. This series of reactions is summarized and exemplified in the following scheme:

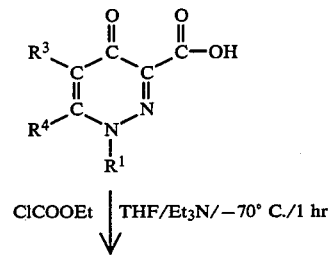

ClCOOEt | THF/Et$_3$N/−70° C./1 hr

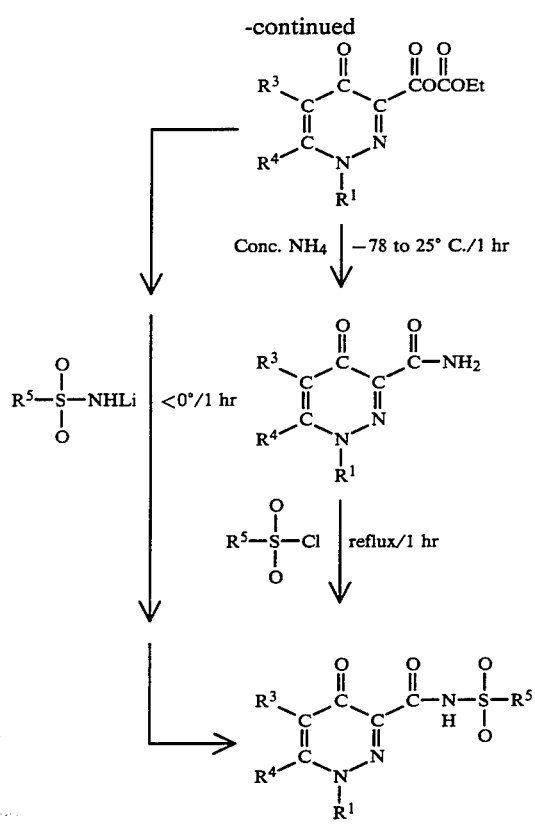

Tetrazoles of the invention can easily be synthesized from a cyano compound formed by dehydrating the carboxamide described in the previous reaction scheme. The cyano group of this compound can easily be converted into a tetrazole by reacting with an azide using known methods, for example by refluxing in acetic acid for from several hours to several days. This reaction is summarized and exemplified in the following reaction scheme:

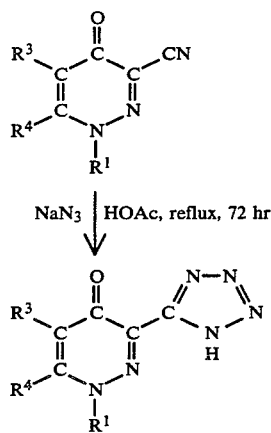

Various modifications of these reactions can be used to produce all the compounds of the present invention, for example as is disclosed in the three prior art patents previously cited (DOS No. 28 08 795, EP No. 37 133, and EP No. 49 971), which are herein incorporated by reference.

Compounds of the invention are useful as chemical hybridization agents in gramineous crops, such as wheat, barley, maze, rice, sorgrum, millet, oats, rye, triticale, forage crops and the like. Of these, wheat is a preferred plant for treatment. Different plant growth regulating effects will be obtained depending upon the growth stage of the plant when treated. Compounds of the invention induce selected male sterility without also inducing unacceptable female sterility. About 30% female fertility is generally acceptable, although this level may differ when the method is used commercially, based on the economics of $F_1$ seed production. As used herein, the term male sterility includes sterility caused by lack of male flower parts, by formation of sterile pollen, and by male flower parts which produce normal pollen but are functionally unable to cause pollination. Where the male sterility of compounds of the invention is accompanied by female infertility of an unacceptable level or by phytotoxicity, the compounds are still minimally useful in production of ergot, for example as described in French Published patent application No. 2400832, which is herein incorporated by reference.

When compounds of the invention are used in hybridization, they are used in an amount sufficient to produce the effect of male sterility without producing a phytotoxic reaction or other undesired side-reaction. Compounds of the invention are generally applied at a rate of from 0.025 to 20.0 pounds per acre, and preferably from 0.125 to 10.0 pounds per acre. The amount used depends upon the plant type and the method of application as is well-known to those skilled in the art and can be determined by simple experimentation if not known.

Although any method of hybridization may be used, the following method generally is sufficient. The two parent strains to be crossed are planted in alternate sections, rows, or groups of rows. The female parent is treated with a compound of the invention in order to render this parent male sterile. Pollen from the male (untreated) parent then fertilizes the female parent, either by means of human intervention or preferably by means of a natural process, such as wind-borne pollination. The seed produced by the female parent is an F-1 hybrid, which is then collected according to convention techniques.

One method of applying the compounds of the invention in the previously-mentioned hybridization technique or for otherwise inducing male sterility is application directly to the plant leaves. When this method is used, very selective male sterility can be obtained when the compound is applied between the beginning of bloom and the beginning of meiosis.

Compounds of the invention can also be applied directly to seed in order to cause male sterility, whereby the seeds are dipped into a fluid formulation containing the active ingredient. Seed can also be sprayed with a solution or suspension containing a compound of the invention. In general, seed are treated with a compound of the invention in an amount of from about ¼ to 10 pounds per 100 pounds of seed. Compounds of the invention are also effective when they are applied to the medium in which plants are grown such as soil or the water surface in a rice field.

Compounds of the invention can be used as hybridization materials together with other plant regulatory agents, for example, in mixtures with these compounds. Examples of plant regulating materials which can be used include auxins, gibberellins, ethylene liberating materials such as Ethephon, pyridones, cytokinins, maleic hydrazide, carbonic acid, 2,2-dimethyl hydrazide, cholines (as well as their salts), (2-chloroethyl)trimethylammonium chloride, triiodobenzoic acid, tributyl-2,4-dichlorobenzenephosphonium chloride, polymeric N-vinyl-2-oxazolidinones, tri(dimethylaminoethyl)-phosphate, and salts of these compounds as well as N-dimethylamino-1,2,3,6-tetrahydrophthalamides and their salts. Compositions containing one or more compounds of the invention in a 1:99-99:1 ratio to one or more different compounds having plant regulatory activities may be prepared. Likewise, compounds of the invention may be prepared into compositions useful for other agricultural purposes, such as herbicides, fungicides, insecticides, and plant bactericides.

A compound of the invention can be applied to a plant either as itself or in combination with other plant growth regulators. A composition containing a compound of the invention and any other active ingredient may be diluted with an agronomically suitable carrier, which is any substance which itself is without any significant effect on plants but which is added in order to allow simpler application of the active ingredients to plants. Carriers include both liquids and solids. Accordingly, compositions of the invention can be either solid or liquid formulations or solutions. For example, the compounds can be used in powders, emulsifiable concentrates, dusts, pellets, aerosols and solutions. In any of the various formulations, a surface active agent may be added in order to increase uptake of the active compounds. It is especially preferred, and particular for methods which involve application to leaves, to utilize agents which aid in the application of the material, for example, dispersion agents and detergents.

Compounds of the invention can be dissolved in any suitable solvent. Examples of solvents which can be used include water, alcohols, ketones, aromatic hydrocarbons, halogenated hydrocarbons, dimethylformamide, dioxane, and dimethylsulfuloxide. Mixtures of these solvents can likewise be used. The concentration of these solutions can be from about 2 to about 98% by weight of active ingredient and is preferred to be in the range from about 20 to about 75% by weight.

In order to produce emulsifiable concentrates, the compounds of the invention are dissolved in an organic solvent, such as benzene, toluene, xylene, methylated naphthalene, corn oil, terpentine, o-dichlorobenzene, isophorone, cyclohexane, or methyl oleate or in mixtures of these solvents, together with an emulsifying material which allows the dispersion in water. Suitable emulsifying agents include ethylene oxide derivatives of alkylphenols or long-chained alcohols, mercaptans, carboxylic acids, and reactive amines, and especially high molecular weight alcohols. Solvent-soluble sulfates or sulfonates, such as the alkaline earth salts or amine salts of alkylbenzenesulfonates as well as sodium fatty alcohol sulfates with surface active properties can be utilized as emulsifying agents either alone or in combination with an ethylene oxide reaction product. Free-flowing emulsion concentrates are formulated similarly to emulsifiable concentrates and contain, in addition to the previously described components, water as well as a stabilizing agent, such as a water-soluble cellulose derivative or a water-soluble salt of a polyacrylic acid. The concentration of the active ingredient in the emulsifiable concentrate is generally about 10 to 60 wt. % and in free-flowing emulsion concentrates is generally about 10 to 60% or sometimes up to 75% by weight.

When a powder containing the compound of the invention is being prepared, the active ingredient is usually mixed with a finely divided solid, such as a clay, an organic silicate or carbonate, or a silica gel along with an agent capable of holding together the resulting materials. The concentration of the active ingredient in such powders generally lies between about 20 and 98% by weight and preferably lies between 40 and 75% by weight. A dispersion material can generally be present in an amount of about 0.5 to 3% by weight of the entire powder. An agent may be added in order to control water absorption and if added is generally present in an amount of about 0.1 to about 5% by weight of the total powder.

Dusts can be prepared by mixing the active ingredient with a finely divided inert solid, which can be of an organic or inorganic nature. Suitable material for this purpose include flour, farina, diatomite, silicates, carbonates, and clays. A satisfactory method for the production of dusts involves crushing a wettable powder together with a finely divided carrier. A dust concentrate, which contains from about 20 to about 80% of the active ingredient, is produced according to known methods and then diluted to form a final concentration of the compound of the invention of about 1 to about 10% by weight of the dust.

Particulate formulations can be prepared by any known method, for example by impregnating the active ingredient into a solid material, such as particulate Fullers earth, vermiculite, cornmeal, seed hulls such as grain hulls, or other materials. A solution of one or more of the compounds of the invention in a freely flowing organic solvent can be applied to the particulate solid or mixed therewith, after which the solvent is evaporated away. The particulate material is not limited to a particular size. However, a useful size is from 16 to 60 mesh (U.S. standard mesh size). The active ingredient generally occupies about 2 to about 15 wt % of the particulate formulation.

Salts of the compounds of the invention can be prepared as aqueous solutions and applied in this form. The salts occupy typically about 0.05 to about 50 wt. % and preferably from about 0.1 to 10 wt. % of the solution. In any event, these solutions may be diluted with additional water prior to use. In some cases the activity of the active material can be increased by including another agent in the solution, such as glycerin, methylethylcellulose, hydroxyethyl cellulose, polyoxyethylene sorbital mono-oleate, polypropylene glycol, polyacrylic acid, polyethylene sodium malanate, or polyethyleneoxide. The auxiliary occupies generally from about 0.1 to about 5 wt. % and particularly from about 0.5 to 2 wt. % of the solution. The various solutions can in any case also contain an agriculturally suitable surface active agent.

The compounds of the invention can be applied according to any known methods, for example in the form of hydraulic sprays, air sprays or dusts. For methods which involve the application of small volumes, a solution of the compound is generally utilized. The volume used and the rate of application depend upon various factors which vary with the method used, such as the specific type of application method, the stage of development of the plant to which the active ingredient is being applied, and other factors well known to those skilled in the art or easily determined by simple experimentation.

Having now generally described this invention, the same will be better understood by reference to certain specific examples which are included herein for purposes of illustration only and are not intended to be limiting of the invention or any embodiment thereof, unless so specified.

Example 1: Synthesis of 1-(4-chlorophenyl)-1,4-dihydro-3-methylsulfonamidocarbonyl-4-oxo-6-methylpyridazine To a mixture of 1.3 g of 1-(4-chlorophenyl)-1,4-dihydro-4-oxo-6-methylpyridazine-3-carboxylic acid and 0.73 ml of triethylamine in 50 ml of THF was added at −40° C., 0.53 ml of ethyl chloroformate, and the resulting mixture was allowed to reach room temperature over 2 hours with continued stirring. The mixture was then cooled to −78° C., and the monolithium salt of methanesulfonamide (prepared from 18 mmole of lithiodiisopropylamide and 15 mmole (1.42 g) of methanesulfonamide) in 25 ml of THF was added dropwise at −65° C. The resulting slurry was allowed to reach room temperature with continual stirring. After an additional hour of stirring the reaction mixture was diluted with 200 ml of ether and washed with 1N hydrochloric acid. The ether layer was then extracted with 5% sodium bicarbonate and the aqueous phase was acidified to pH2. The resulting precipitate was collected by filtration and recrystallized from methanol to yield 1.206 g of product, m.p. 225°-227°.

Example 2: Biological Activity

A biological assay for pollen suppression was conducted on the wheat variety W-41 (Anza). This is a heavy tillering wheat which is grown commercially in California. Seeds were planted to provide four plants per 8-inch pot. Plants were raised in a greenhouse until the stage indicated in the following table of results. Three different stages of growth were defined for the purposes of this experiment as follows: Stage 1, spike length of 0.1–0.5 cm; Stage 2, spike length of 0.5–1.5 cm; Stage 3, spike length of 1.5–2.5 cm. External appearance was correlated with the development of the spikelet in order to avoid mistaking the onset of meiosis. Spikelets were removed at various developmental stages and anthers were removed from the most mature florets (which generally occured in about the middle of the spiklet). The anthers were crushed in acetocarmine or propeocarmine and the state of pollen development was assessed. Cytological examinations were made to assess the best time for application. Compounds were applied as solutions in water or water/acetone (5–50% acetone) or as aqueous emulsions. In all cases, 0.1% Triton X-100 was used as a wetting agent. Plants were sprayed to runoff with a test solution and then replaced in such a way that control plants were interspersed with treated plants. Heads were bagged upon emergence and seed set was used as a measure of sterility induction. Compounds that demonstrated good sterilization ability were tested for their effect on female fertility by cross-pollination of awned female plants with awnless male pollen donors.

Control studies were conducted using a known prior art compound (1-(4-chlorophenyl)-1,4-dihydro-4-oxo-6-methylpyridazine-3-carboxylic acid). Optimal dosage and correct stage of application of this compound were determined in order that test crosses could be compared to test crosses made using the compounds of the invention.

Using the general procedure described above, 1-(4-chlorophenyl)-1,4-dihydro-3-methylsulfonamidocarbonyl-4-oxo-6-methylpyridazine was screened for pollen suppressing activity.

| Results of Biosaasy | | |
|---|---|---|
| Stage of Application | Dose (ppm) | % of Sterility |
| 2 | 2000 | 100 |
| 2 | 750 | 61.6 |
| 2 | 500 | 39.0 |
| 2 | 250 | 14.7 |

The invention now being fully described, it will be apparent to one of ordinary skill in the art that many changes and modifications can be made thereto without departing from the spirit or scope of the invention as set forth herein.

What is claimed as new and desired to be secured by Letters Patent of the United States:

1. A pollen suppressant of the formula

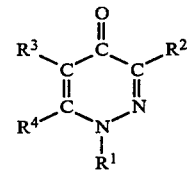

wherein
R$^1$ and R$^4$ independently represent C$_1$–C$_4$ alkyl, phenyl, naphthyl, or phenyl or naphthyl substituted with one to three substituents selected from the group consisting of halogen, trihalomethyl, C$_1$–C$_4$ alkoxy, C$_1$–C$_4$ alkyl, and cyano;
R$^2$ is

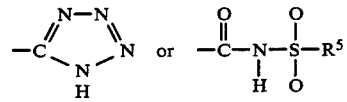

wherein
R$^5$ is C$_1$–C$_{12}$ alkyl and may further be substituted with one or more halogens, or aryl selected from the group consisting of 6-membered rings containing 0–3 nitrogens and fused bicyclic 10-membered rings containing 6 atoms in each ring and 0–3 nitrogens per ring with the remaining atoms in the ring or rings of said aryl group being carbon atoms, said aryl group being optionally substituted with C$_1$–C$_4$ alkyl or an electron-withdrawing group selected from the group consisting of nitro, carboxy, COR$^6$, CHO, COOR$^6$, halogen, CONR$^6$R$^7$ and cyano; and
R$^3$ is hydrogen, halogen, C$_1$–C$_4$ alkyl, carboxy or an agronomically acceptable alkali metal salt thereof, or a group of the formula —COOR$^6$ or —CONR$^6$R$^7$, wherein R$^6$ is C$_1$–C$_4$ alkyl, and R$^7$ is R$^6$ or hydrogen.

2. The pollen suppressant of claim 1, wherein R$^1$ is phenyl or phenyl substituted with 1 to 3 substituents selected from the group consisting of halogen, trihalomethyl, C$_1$–C$_4$ alkoxy, C$_1$–C$_4$ alkyl, and cyano.

3. The pollen suppressant of claim 2, wherein R$_1$ is phenyl substituted with one substituent selected from the group consisting of halogen and trihalomethyl.